United States Patent [19]

Lince Lalinde, deceased

[11] 4,150,119

[45] Apr. 17, 1979

[54] METHOD FOR TREATMENT OF VASCULAR DISEASE

[75] Inventor: Ernesto Lince Lalinde, deceased, late of Medellin, Colombia, by J. Emilio Lince Isaza, legal representative

[73] Assignees: Jesus Emilio Lince Isaza; Aracely Munoz de Lince; Leonardo Lince Mora, all of San Antonio, Tex.

[21] Appl. No.: 760,167

[22] Filed: Oct. 22, 1976

[51] Int. Cl.$^2$ .............................................. A61K 33/32
[52] U.S. Cl. ...................................................... 424/144
[58] Field of Search .......................................... 424/144

[56] References Cited

U.S. PATENT DOCUMENTS

| 98,690 | 1/1870 | Grigg | 424/144 |
|---|---|---|---|
| 371,590 | 10/1887 | Kincaid | 424/144 |

OTHER PUBLICATIONS

The National Dispensatory, Apr. 1879, published Phila., Pa., pp. 1137 & 1138.
Gruber, "Handbook of Treatment & Medical Formulory", published by F. A. Davis Co., Phila. Pa. (1949), pp. 95, 229, 230, 236, 369, 403 & 429.

Primary Examiner—Donald B. Moyer
Attorney, Agent, or Firm—Arnold, White & Durkee

[57] ABSTRACT

The instant invention relates to a method for treating vascular disease comprising the administration by deep intramuscular injection to a patient suffering from said disease of an amount of a dilute aqueous solution of potassium permanganate effective for treating said disease.

11 Claims, No Drawings

METHOD FOR TREATMENT OF VASCULAR DISEASE

BACKGROUND OF THE INVENTION

This invention relates to a method for treatment of vascular diseases. More particularly, this invention relates to a method for treating vascular diseases comprising administration by deep intramuscular injection to a patient suffering from said disease of an amount of a dilute aqueous solution of potassium permanganate effective for treating said disease.

The major cause of death in the United States and most industrialized societies is arterial degeneration. The major share of this degeneration is attributable to arteriosclerosis, a generic term for thickening and induration of the arterial wall. One type of arteriosclerosis is atherosclerosis which is a vascular disease characterized by the formation of focal intimal atheromas.

As this disorder, atherosclerosis, progresses the atheromas undergo a variety of complications, (e.g., calcification, internal hemmorhages, ulceration and sometimes superimposed thrombosis). The primary significance of these arterial lesions resides in their potential to produce stenosis and occlusion. Thus, arteriosclerosis is almost always the cause of myocardial infarction, cerebral vascular accident and vascular diseases of the lower extremities.

The following influences have been identified as contributing to the incidence and severity of atherosclerosis in vulnerable populations: high total calorie intake, high animal fat intake, high carbohydrate intake, elevated blood sugar levels, obesity, hypertension, sedentary occupation, a driving personality structure, a stressful life, and cigarette smoking (Morris, J. N., and Gardner, M. J.: EPIDEMIOLOGY OF ISCHEMIC HEART DISEASE. AM. J. MED. 46: 647, 1969).

The medical profession is sharply divided over the control of atherosclerosis by modification of the diet and blood lipid levels. In general, most of the diet modifications take the form of lowering the total caloric intake, lowering fat intake, substituting polyunsaturated dietary fat for saturated fat and restriction of carbohydrate intake.

Prevention, rather than treatment, has been the goal since no evidence has been obtained in humans that atherosclerosis lesions can be made to regress.

As previously indicated, atherosclerosis has been found to be a cause of vascular diseases of the extremities; however, there are other causes. Sudden interruption of the blood supply to all or a portion of an extremity results in a spectrum of symptoms and signs which are dependent upon the location and extent of the occlusion and immediately available alternative circulatory routes. The major causes of acute arterial occlusion are embolism, thrombosis and injury. In the upper extremity the heart is the source of the emboli in an overwhelming majority of the patients with this problem. In the lower extremity over half of emboli will lodge in either the superficial femoral or the popliteal artery, the abdominal aorta, iliac arteris or the three major vessels distal to the popliteal artery may become occluded.

When acute arterial occlusion involves a critical segment of the arterial system and the potential for collateral circulation is poor the following symptoms are indicated: complaints of pain in the most distal part of the limb, this pain complaint is accompanied by pallor, coldness and a sensation of numbness. Subcutaneous hemorrhage, focal gangrene, and fixed staining of the skin develop within a relatively short period of time.

In situations where the collateral circulation is poor or inadequate, immediate operation has been required because of the high incidence of limb loss and subsequent disability if nonoperative treatment is employed. The surgical treatment may include one of the following: endarterectomy, embolectomy, thromboembolectomy, sympathectomy, bypass graft, or replacement of artery or arteries.

In advanced arterial insufficiency cases, surgical treatment failure may lead to the loss of a limb due to ischemia or gangrene or, in the most advanced cases, it may lead to death. In some cases treatment may consist of administration of anticoagulants, vasodilators, steroids, analgesics and sympathetic blocks together with dietary control; however, results are generally poor.

Other vascular diseases which may be treated by surgical treatment include gangrene, Buerger's disease (thromboangiitis obliterans), varices Raynaud's disease endarteritis obliterans, varicose ulcers, arterial thrombosis, venous thrombosis, varicose veins, ischemic ulcers and arteritis.

Surgical treatment in many cases is contraindicated as for example with patients suffering from diabetes mellitus and gangrene of an extremity. In these cases, amputation is quite commonly the only alternative. For cases such as these, and others as will become apparent to those skilled in the art, this invention provides an attractive alternative.

SUMMARY OF THE INVENTION

This invention relates to a method for treating vascular diseases which comprises the administration of an aqueous solution of $KMnO_4$, potassium permanganate.

Historically, aqueous solutions of potassium permanganate have been used medicinally as an antiseptic and deodorizing application to foul ulcers, cancer and ozena. Further, said aqueous solutions have been utilized as a gastric lavage in poisoning by morphine, strychnine, aconite and picrotoxine. To applicant's knowledge, others have not utilized potassium permanganate in the manner specified in this application.

DESCRIPTION OF SPECIFIC EMBODIMENTS

The invention relates to a method for treating vascular disease comprising administration by deep intramuscular injection to a patient suffering from said disease of an amount of a dilute aqueous solution of potassium permanganate effective for treating said disease.

Potassium permanganate is a dark purple crystal which has a molecular weight of 158.03 g/g-mole and a specific gravity of 2.7032. Potassium permanganate is a powerful oxidizing agent which has a sweetish, astringent taste and which is odorless. Is it soluble in water and in alcohol. A concentrated solution of potassium permangamate has a deep violet-red color and when highly diluted has a pink color. Extreme care should be observed in handling potassium permanganate as explosions may occur when it is contacted with organic or other readily oxidizable substances.

More particularly, treatment in accordance with this invention, is comprised of the injection of dosages of a dilute aqueous solution of potassium permanganate wherein each of said dosages consist of from 20 to 25 milligrams of potassium permanganate and wherein the total amount of potassium permanganate injected during said treatment is from about 600 to 1800 milligrams.

In some extreme cases, the patients are not completely cured after the administration of up to 1800 milligrams of the dilute aqueous solution of potassium permanganate. In those cases, the patient may be administered additional dosages of said solution periodically in sufficient amounts so as to alleviate the pain associated with the particular vascular disease.

The deep intramuscular injection of the dilute aqueous solution of potassium permanganate is quite painful; therefore prior to that injection a local anesthetic is utilized to assuage the resulting pain. Despite the preference in using a local anesthetic, it is not required for effective treatment of vascular diseases in accordance with the invention herein described.

An example of potassium permanganate which may be utilized in the practice of the instant invention is that sold by Eli Lilly Laboratories and which conforms to USP standards. Typically, one gram of such potassium permanganate is admixed with 100 cubic centimeters of boiled or distilled water to formulate a one percent solution of potassium permanganate.

The local anesthetic utilized in alleviating the pain of the injection of the dilute solution of potassium permanganate may be selected from a group of many such anesthetics available. For example, Xylocaine sold by Astra and Novocain sold by Winthrop may be utilized as local anesthetics. Typically, for example with Xylocaine, 2 CC of a 1 or 2% solution may be utilized as the anesthetic. (It should be cautioned that epinephrine should not be utilized with any of the anesthetics when anoxia is indicated due to the possibility of ventricular fibrillation.)

In the preferred embodiment, the treatment consists of from 30 to 60 deep intramuscular injections of a one percent aqueous solution of potassium permanganate wherein each deep intramuscular injection is comprised of a dosage of from 20 to 25 milligrams of potassium permanganate, said dosage dependent on the size of the patient and severity of the disease. Prior to injection of each dosage of said aqueous solution of potassium permanganate, a patient is injected with 2 cubic centimeters of a local anesthetic selected from the group of Novocain or Xylocaine. It is desirable to inject a patient deep intramuscularly in the gluteal area due to better absorption of the medication and to avoid severe irritation of the tissues from the potassium permanganate injection.

As previously stated, the length of treatment, i.e., the number of dosages required depends upon the size of the person and the severity of the disease. Typically the total potassium permanganate injected during the treatment ranges from 600 to 1800 milligrams.

It should be appreciated by those skilled in the art that during the period of treatment the patient should avoid use of alcohol, tobacco products and antibiotics.

The method of the preferred embodiment has been utilized in treating gangrene, Buerger's disease, varices, Raynaud's disease, endarteritis obliterans, varicose ulcers, arterial thrombosis, venous thrombosis, varicose veins, ischemic ulcers and arteritis. This list is not intended to be exhaustive of all vascular diseases for which this invention may be utilized in treating.

It should also be appreciated that in view of the results obtained in the treatment of other diseases the method of this invention may potentially be useful in the treatment of myocardial infarction, coronary artery disease, pulmonary emboli, pulmonary infarction, collagen disease, cerebral thrombosis, diabetes mellitus, frost bite, and trench foot.

The invention disclosed herein has been utilized in South America, particularly in Colombia, for the treatment of vascular disease. The method has remained a secret since its discovery approximately fifty years ago.

The invention was first injected into a close relative of the inventor who suffered from gangrene secondary to thomboangiitis obliterans. The results led the inventor to improve the formula which has since been utilized in treating many vascular diseases in many different patients in Colombia.

The following discussion of case histories of patients treated according to the invention disclosed herein serves to illustrate the procedure employed in utilizing the teachings of the instant invention.

Case History #1:

The patient's right leg was ischemic; he complained of pain in that leg; and his right foot's temperature was lower than normal. The toes of both feet appeared pale and felt cold. The patient could not walk without the use of crutches.

Treatment in accordance with this invention was initiated; the patient was administered one (1) injection of a dilute aqueous solution of potassium permanganate intramuscularly every 24 hours for four days per week. This was followed by three days per week of rest without injections. Each dose was 2 cubic centimeters of a 1% aqueous solution of potassium permanganate. The patient was administered four (4) injections (dosages) weekly for sixteen (16) weeks; 20 mg of $KMnO_4$ per dosage was administered for a total of 1280 mg of $KMnO_4$ for the 16 week treatment period.

After eight weeks of treatment, the patient was able to walk without crutches. Normal temperature and color were restored to both feet and the patient no longer complained of pain in his right leg. After sixteen (16) weeks of treatment the patient was able to return to his normal occupation.

During the treatment some febrile reaction was observed; however, no other ill effects were apparent. Oscillometric measurements were made both before and shortly after treatment in accordance with this invention. The results are recorded in Table I.

TABLE I

| Location | Oscillometric Measurements | |
| --- | --- | --- |
| | Before | After |
| Popliteal | 1 | 6 |
| Popliteal bifurcation (below knee) | 1 | 6 |
| Posterior Tibial | 0 | 2 |
| Dorsolis Pedis | 0 | ½ |

Case History #2:

The patient complained of severe pain in the left leg; his left foot felt cold. Intermittent claudication developed after walking approximately 200 meters. In addition, the patient appeared to be extremely nervous.

The patient was treated in the same manner as the patient in Case History #1 above. After 16 weeks, the patient returned to his normal activities and he was able to walk five (5) kilometers without any evidence of claudication. The patient recovered without any apparent ill effects or sequela.

Oscillometric measurements were made both before and after the treatment and the results are set out in Table II.

TABLE II

| | Oscillometric Measurements | |
|---|---|---|
| Location | Before | After |
| Popliteal | 5 | 11 |
| Popliteal bifurcation | 5 | 10 |
| Posterior Tibial | 2 | 4 |
| Dorsolis Pedis | 0 | 1 |

Case History #3:

Prior to the patient's treatment in accordance with the invention disclosed herein, the patient had undergone three (3) sympathectomy operations on his legs. [two (2) on his right side and one (1) on his left side]. The patient had also undergone eight (8) denervation of the arteries operations on his right leg prior to his treatment in accordance with this invention.

The patient complained of extreme pain in his right foot due to severe ischemia of the right leg and foot. His right foot was cyanotic and he was unable to walk or stand on it.

The patient was treated in the same manner as the patient in Case Histories numbers 1 and 2 above except his treatment was over an 18 week period (72 injections) for a total of 1440 mg $KMnO_4$. About the fourth week of treatment the patient complained less of pain and the temperature of the right foot increased. During the eighth (8th) week of treatment the pallor of the right foot began to disappear. After the twelfth (12th) week, he was able to stand on the right foot and walk with a crutch. After a total of 72 injections (18 weeks), the treatment was terminated and no ill side effects were noted other than a febrile reaction.

Oscillometric measurements were taken both before and after the treatment and the results are recorded in Table III.

TABLE III

| | Oscillometric Measurements | |
|---|---|---|
| Location | Before | After |
| Popliteal | 3 | 8 |
| Popliteal bifurcation | 2 | 6 |
| Posterior Tibial | 1.5 | 3 |
| Dorsolis Pedis | 0 | 1 |

Case History #4:

This patient, prior to her treatment in accordance with this invention, had developed severe Raynaud's disease with marked cyanosis of the fingers of both hands and extreme pain. Her doctors advised her that amputation would be inevitable; however, as a last resort she was advised to receive treatment in accordance with this invention.

The patient was treated in the same manner as those patients in Case Histories numbers 1, 2 and 3 above except this patient was treated for approximately 12 weeks. During the treatment her condition improved and by the end of the treatment a complete regression of the symptoms was indicated by restoration of circulation in the hands and fingers. In addition, cyanosis and pallor of the fingers, as well as stiffness of the fingers completely disappeared. This patient showed no signs of ill effects from the treatment, she resumed normal activities.

In view of the preceding description of the invention, further modifications and alternative embodiments of the method will be apparent to those skilled in the art. Accordingly, the preceding description is to be construed as explanatory and illustrative only and is for the purpose of teaching and enabling those skilled in the art to treat vascular diseases. While the preferred embodiment of the above described invention is to be understood to be the best mode presently contemplated, it is by no means the only embodiment possible. The scope of the invention is defined by the following claims and also by all equivalent modifications and variations that fall within the true spirit of the invention.

What is claimed is:

1. A method for treating cyanosis of the extremities comprising administration by deep intramuscular injection to a patient suffering from said disease of an amount of a dilute aqueous solution of potassium permanganate effective for treating said disease.

2. The method of claim 1 wherein said treatment is comprised of the injection of dosages, each of said dosages consisting of from 20 to 25 milligrams of potassium permanganate.

3. The method of claim 2 wherein the total amount of potassium permanganate injected during said treatment is from about 600 to about 1800 milligrams.

4. The method of claim 3 where said dilute aqueous solution is a one percent aqueous solution.

5. The method of claim 4 comprising the additional step of anesthetizing said patient with a local anesthetic prior to and in the same body region as said injection.

6. The method of claim 5 wherein said anesthetizing step comprises the administration of either Xylocaine or Novocain by deep intramuscular injection in an amount effective to relieve said patient of the pain resulting from said injection of a dilute aqueous solution of potassium permanganate.

7. A method for treating cyanosis of the extremities comprising administration by deep intramuscular injection to a patient suffering from said disease of a one percent aqueous solution of potassium permanganate in dosages of from 20 to 25 milligrams of potassium permanganate.

8. The method of claim 7 wherein the total amount of potassium permanganate injected during said treatment is from about 600 to about 1800 milligrams.

9. The method of claim 7 comprising the additional step of anesthetizing said patient with a local anesthetic prior to and in the same body region as said injection.

10. The method of claim 8 wherein said anesthetizing step comprises the administration of either Xylocaine or Novocain by deep intramuscular injection in an amount effective to relieve said patient of the pain resulting from said injection of potassium permanganate.

11. A method for treating cyanosis of the extremities comprising the steps of:
 (a) administration in the gluteal area of the body by deep intramuscular injection of a local anesthetic,
 (b) administration by deep intramuscular injection in the gluteal area of a one percent aqueous solution of potassium permanganate in dosages of from 20 to 25 milligrams of potassium permanganate wherein the total amount of potassium permanganate injected during the treatment is from about 600 to about 1800 milligrams, and each injection of said local anesthetic is in an amount effective to relieve said patient of the pain resulting from said injection of potassium permanganate.

* * * * *